(12) United States Patent
Winthrop (10) Patent No.: US 9,480,808 B2
(45) Date of Patent: Nov. 1, 2016

(54) TRACHEOSTOMY DEVICES AND METHODS OF USE

(71) Applicant: Neil T Winthrop, West Palm Beach, FL (US)

(72) Inventor: Neil T Winthrop, West Palm Beach, FL (US)

( * ) Notice: Subject to any disclaimer, the term of this patent is extended or adjusted under 35 U.S.C. 154(b) by 314 days.

(21) Appl. No.: 13/951,412

(22) Filed: Jul. 25, 2013

(65) Prior Publication Data
US 2014/0026891 A1    Jan. 30, 2014

Related U.S. Application Data

(60) Provisional application No. 61/675,393, filed on Jul. 25, 2012.

(51) Int. Cl.
| | |
|---|---|
| *A61M 16/00* | (2006.01) |
| *A61M 25/00* | (2006.01) |
| *A61M 16/04* | (2006.01) |
| A61M 25/02 | (2006.01) |

(52) U.S. Cl.
CPC ........ *A61M 16/0497* (2013.01); *A61M 16/047* (2013.01); *A61M 16/0434* (2013.01); *A61M 16/0488* (2013.01); *A61M 2025/0273* (2013.01)

(58) Field of Classification Search
CPC .................... A61M 16/0497; A61M 16/0463; A61M 16/0465; A61M 16/047; A61M 16/0488; A61M 2025/0273
See application file for complete search history.

(56) References Cited

U.S. PATENT DOCUMENTS

| | | | | |
|---|---|---|---|---|
| 4,156,428 A * | 5/1979 | Henkin | ............. | A61M 16/0479 128/207.15 |
| 4,240,417 A * | 12/1980 | Holever | ............ | A61M 16/0465 128/203.12 |
| 5,749,360 A * | 5/1998 | Lacey | ................. | A61M 16/047 128/200.26 |
| 6,024,730 A * | 2/2000 | Pagan | ............... | A61M 25/0054 604/264 |
| 6,174,320 B1 * | 1/2001 | Kugel | ................... | A61F 2/0063 606/151 |
| 8,979,812 B2 * | 3/2015 | Loescher | ................ | A61F 5/443 604/338 |
| 2010/0331785 A1 * | 12/2010 | Fabo | ................... | A61M 16/047 604/180 |

* cited by examiner

*Primary Examiner* — Bradley Philips
(74) *Attorney, Agent, or Firm* — John M. Behles (57) ABSTRACT

Tracheostomy devices and methods of use are provided herein. An exemplary device may include a substrate having an opening that is disposed centrally on the substrate, the opening being configured to receive a connector of a tracheostomy tube, the substrate comprising a plurality of mounting holes disposed on opposing ends of the substrate, the substrate having a slit that extends below the opening which allows the substrate to be removed from the connector when the connector is connected to an airway hose.

6 Claims, 6 Drawing Sheets

TRACHEOSTOMY DEVICES AND METHODS OF USE

CROSS REFERENCE TO RELATED APPLICATIONS

This non-provisional U.S. patent application claims the priority benefit of U.S. Provisional Application Ser. No. 61/675,393, filed on Jul. 25, 2012, which is hereby incorporated by reference herein in its entirety including all references cited therein.

FIELD OF THE INVENTION

The present technology relates generally to tracheostomy devices and methods of use, and more specifically, but not by way of limitation, to various tracheostomy tube holders that provide an improved mechanism to secure the tube to the patient at an optimal position and orientation.

SUMMARY

According to some embodiments, the present technology may be directed to a tracheostomy support device comprising a substrate having an opening that is disposed centrally on the substrate, the opening being configured to receive a connector of a tracheostomy tube, the substrate comprising a plurality of mounting holes disposed on opposing ends of the substrate, the substrate comprising a slit that extends below the opening which allows the substrate to be removed from the connector when the connector is connected to an airway hose.

According to some embodiments, the present technology may be directed to a tracheostomy support device comprising: (a) a substrate comprising: (i) a first side having a first opening that receives a tube of a tracheostomy tube, wherein the first side comprises a first slit that divides the first side into two sections; (ii) a second side having a second opening that is disposed centrally on the second side, the second opening being configured to receive a connector of the tracheostomy tube, the substrate comprising a plurality of mounting holes disposed on opposing ends of the second side, the second side comprising a second slit that extends below the second opening which allows the substrate to be removed from the connector when the connector is connected to an airway hose; and (iii) wherein the first and second sides are attached to one another in such a way that the first side can be folded and overlapped around a plate of the tracheostomy tube.

BRIEF DESCRIPTION OF THE DRAWINGS

Certain embodiments of the present invention are illustrated by the accompanying figures. It will be understood that the figures are not necessarily to scale and that details (e.g., dimensions) not necessary for an understanding of the invention or that render other details difficult to perceive may be omitted. It will be understood that the invention is not necessarily limited to the particular embodiments illustrated herein.

DETAILED DESCRIPTION OF EXEMPLARY EMBODIMENTS

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

A tracheostomy tube generally refers to a tube or catheter inserted into the trachea of a patient for the purpose of establishing and maintaining an open airway for the patient. Numerous types of tracheal tubes are available, depending on the desired application. One exemplary tracheal tube is the tracheostomy tube. The tracheostomy tube is inserted into a tracheotomy stoma in order to permit the patient to breathe without the use of their nose or mouth. The tracheostomy tube includes a relatively short (two to four inches) curved tube or cannula with a balloon cuff located at a distal end. The balloon cuff is inserted into the patient's trachea and serves to open the patient's airway. It is noteworthy that some tracheostomy tubes may not include a cuff. The tracheostomy tube additionally includes a connector/adapter and a neck plate located near the proximal end. The connector adapter is configured for connection with additional hosing, e.g., connected to an oxygen source. The neck plate rests against the patient's neck and serves as a securing mechanism for the tracheostomy tube. The neck plate generally includes elongated holes on opposing ends, lateral with respect to the stoma. Trach ties (e.g., elastic or fixed straps with Velcro™ on one or each end) may be wrapped around the back of the patient's neck, inserted through the elongated holes on the neck plate, and secured using the Velcro™ so as to secure the tracheostomy tube.

However, the elongated holes of the neck plate do not generally permit sufficient support regarding the proper placement and orientation of the tracheostomy tube. As would be understood, the position/orientation of the tracheostomy tube within the trachea of the patient is a critical factor to ensure an open, unobstructed airway. The trach ties often move around (e.g., slide up and down within the elongated holes) during use, thus permitting the position or orientation of the tracheostomy tube to shift. Differences between the size of the patient's neck may increase the movement of the trach ties within the elongated holes of the neck plate. Such size difference may even further prevent proper placement or orientation of the tracheostomy tube. That is, the size and even general shape (e.g., fatty tissue folds for obese patients) may prevent the trach ties securing the tracheostomy tube from being initially secured in an optimal position or orientation.

Thus, there is a need for tracheostomy tube holders that improves the ability to secure the tube in the patient at an optimal position or orientation so as to ensure an open, unobstructed airway and to prevent subsequent movement of the tracheostomy tube.

Figure 1:
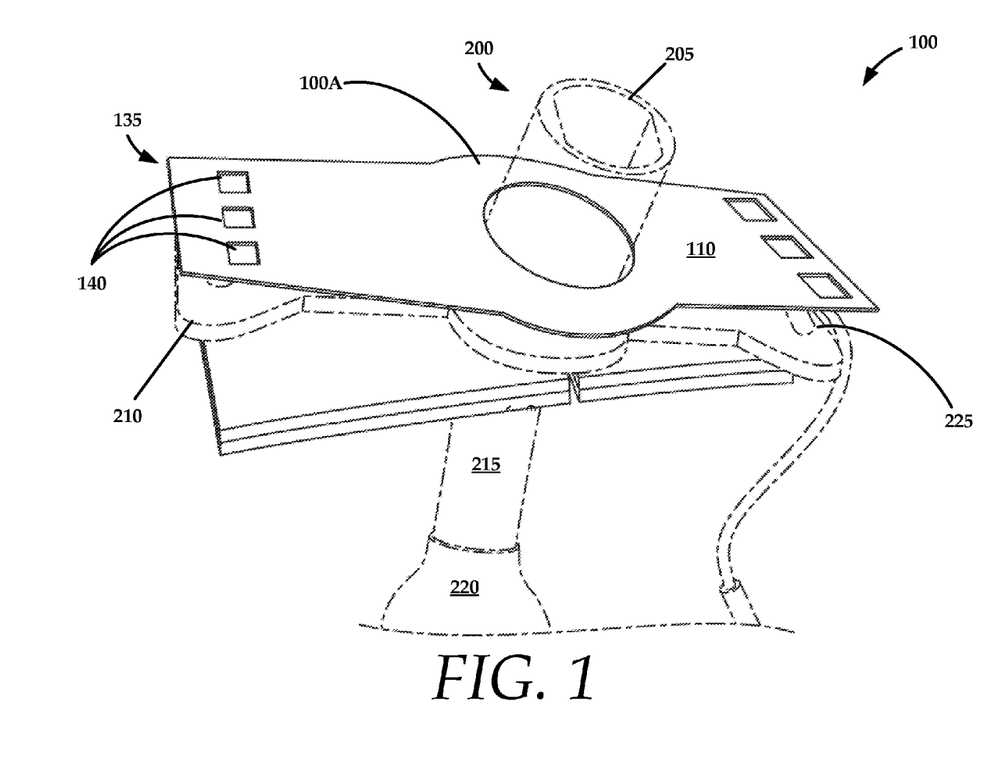
FIG. 1 is a perspective view of an exemplary tracheostomy support device installed on a tracheostomy device, constructed in accordance with the present disclosure.
Figure 2:
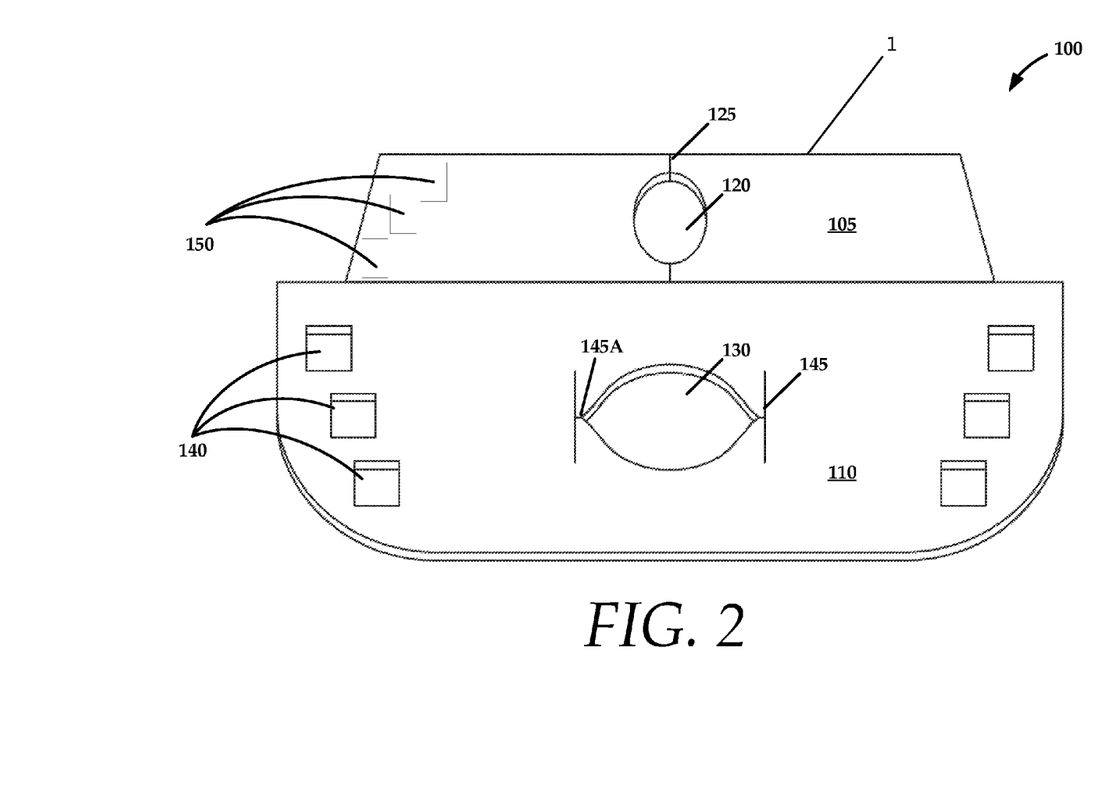
FIG. 2 is another perspective view of an exemplary tracheostomy support device of FIG. 1 without the tracheostomy device.

Referring to FIGS. 1 and 2 now, shown therein are differing aspects of an exemplary tracheostomy tube holder 100 constructed in accordance with the present disclosure. The holder 100 may be utilized in conjunction with existing tracheal tubes (e.g., tracheostomy tubes) in order to provide a low cost mechanism wherein the tracheostomy tube can be secured to the patient at an optimal position and orientation and which minimizes movement of the tracheostomy tube during use. Certain aspects may provide for the holder 100 to be applied to a plate of a tracheostomy tube (e.g., a neck plate portion of a tracheostomy tube) wherein the holder 100 is used to secure the tracheostomy tube to the patient using, for example, trach ties. At least a portion of the holder 100 may be sized/shaped so as to correspond to, and align with the elongated holes of the plate and may further comprise a plurality of mounting holes in said corresponding sections. The user may selects one of the mounting holes in the holder 100 so as to initially achieve the optimal position and orientation for the tracheal tube. For example, a user may select an uppermost mounting hole to be used with the trach tie so as to pull and secure the tracheostomy tube in a desired first direction/orientation. The user may select a lower mounting hole within the holder 100 to pull the tracheostomy tube in a second desired direction/orientation. As another example, the user selecting an uppermost mounting hole on one side and then a lower mounting hole on the opposing side of the holder 100 to permit the user to position/orient the holder 100 at a variety of positions/orientations so as to achieve optimal results. As can be seen, the holder 100 including the plurality of mounting holes on each side provides an improved mechanism wherein the tracheostomy tube can be securely mounted in a wide variety of positions/orientations and can further prevent movement of the tracheostomy tube during use. Generally, the holder 100 may be constructed as a unitary piece and include cutouts, slits, openings, etc., as appropriate, that are sized, shaped, and otherwise configured to securely fit around the components forming the tube, (e.g., to fit around a throat plate portion of a tracheostomy tube).

The tracheostomy tube holder 100 may be used with a tracheostomy tube 200, in accordance with aspects of the present disclosure. As would be understood in the art, the tracheostomy tube 200 may include a connector 205, a plate 210, a tube 215, and a cuff 220. The plate 210 includes elongated holes 225 positioned on opposing sides, i.e., lateral with respect to the tube. The holder 100 may be sized and/or shaped such that the mounting holes 140 are positioned outside the edge of the plate 210 once installed on the tube 200. Said positioning provides a variety of mounting options for the user, such as is described above, rather than the single option available when using the plate 210 with the elongated holes 225. The user may select the mounting holes 140 on opposing sides of the holder 100 depending on the desired position and/ or orientation of the tube 200 yielding an optimally unobstructed airway. As discussed below, the user may use a trach tie 310, such as those illustrated in FIG. 3B. The user may feed opposing ends of the trach tie 310 through the desired mounting holes 140 and then secure the trach tie 310 using Velcro, for example, so as to secure the tracheostomy tube 200 to the patient. As is shown clearly in FIG. 3B, the connector 205 may be connected to an airway hose 315 that is in turn connected to an oxygen system (not shown). Note that FIG. 3B only shows a portion of an airway hose, but that one of ordinary skill in the art would be familiar with the use of such devices.

As shown more clearly in FIGS. 1-2, the holder 100 may comprise a substrate 100A that includes a first side 105 and a second side 110. In use, the first side 105 may be positioned on an inside of the plate of a tracheostomy tube 200 so as to rest against the skin of the patient wherein the second side 110 may be positioned on the outside of the plate of the tracheostomy tube. In accordance with certain embodiments, the first and second sides 105 and 110 may be formed as a single, unitary piece. In this embodiment, the first and second sides 105 and 110 may be configured to fold along a line 115 so as to cover the plate of the tracheostomy tube. The line 115 may include a series of perforations, cutouts, compressions, etc., that permits the holder 100 to be folded along said line. In accordance with other aspects, another embodiment of the holder 100 may provide for the first and second sides 105 and 110 to be constructed as individual pieces wherein they may be connected together via Velcro, tape, a series of tabs, adhesives, etc. In other embodiments, only the second side 110 may be utilized (see FIGS. 3A and 3B).

The first side 105 may comprise a first opening 120 and a cut or slit 125. The first opening 120 may be sized and shaped so as to accommodate and be positioned around the tracheostomy tube 200 during installation such that the first side 105 sets flush against the inside face of a plate 210. The slit 125 may be configured to permit the first side 105 to be positioned on the inside of the plate 210, i.e., the slit 125 may permit the first opening 120 to be opened to accommodate the tube during installation and then to be closed to cover the inside portion of the plate 210 during use. The slit 125 may be formed during construction or may be formed using a plurality of perforations to permit the user to open the slit 125 as needed.

The second side 110 may comprise a second opening 130. The second opening 130 may be sized and shaped so as to fit around the connector portion 205 of the tracheostomy tube 200. That is, during operation the user may insert the connector of the tracheostomy tube 200 into the second opening 130 so as to slide the second side 110 down flush against the outside face of the plate of the tracheal tube 215. The user may then fold the first side 105 along the line 115 so that the first side 105 sets against the inside face of the plate 210 wherein the slit 125 and first opening 120 permit the first side 105 to slide around and accommodate the inside portion of the tube.

Additional aspects may provide for the second side 110 to be wider than the first side 105 so as to define a securing wing 135 positioned at opposing sides of the second side 110 (see FIG. 1). The second side 110 and/or the wings 135 may generally be sized and shaped so as to conform to and align with the elongated holes on the plate of the tracheostomy tube. Additionally, the securing wings 135 may comprise a plurality of mounting holes 140 (with three mounting holes 140 being shown on each wing 135 by way of example). The mounting holes 140 may be sized and/or shaped so as to be used in conjunction with the trach ties to secure the tracheostomy tube to the patient at an optimal position and orientation. The mounting holes 140 aligning with the elongated holes of the plate may provide a wide variety of mounting options for a user. The user may utilize the trach ties connected to differing mounting holes 140 depending on such considerations as the size/shape of the patient's neck, the desired position/orientation of the tracheostomy tube to achieve an unobstructed airway, etc. The mounting holes 140 may further operate to improve the function of the trach ties (e.g., prevent the trach ties from sliding within the elongated holes), thus providing even greater security with regards to the position and orientation of the tracheostomy tube 200 during use.

Although generally shown in FIGS. 1-3B as being square, the mounting holes 140 may be formed using other shapes (round, triangle, rectangle, etc.) which may be used in conjunction with the trach ties. Further, although three mounting holes 140 are shown in each wing 135, the wing 135 may be constructed to comprise two, three, four, five, six, etc., mounting holes 140. Other aspects may provide for the wings 135 to include a plurality of perforated sections wherein the user may form the mounting holes 140 by removing portions of the wings 135 using said perforations.

It is to be understood that the mounting holes may be linearly aligned, such as shown in FIGS. 1-2. However, other aspects may provide for the mounting holes to be offset from each other so as to provide for even further mounting options for the tracheostomy tube (see FIGS. 4 and 5, for example). As would be understood, the mounting holes 140 being offset may provide even further options for a user of the holder 100. For example, the offset mounting holes 140 may provide even further configurations for the user to secure the tracheostomy tube 200 to patients having different sized and/or shaped necks or heads.

Although the second side 110 has herein been described as being wider than the first side 105 via, for example, the securing wings 135, it is to be understood that the first and second sides 105 and 110 may be the same size. When the first and second sides 105 and 110 are the same size/shape, the first side 105 may additionally include a plurality of mounting holes 150 (see FIG. 2) that are sized and positioned so as to align with the mounting holes 140 of the second side 110. As such, the user would insert the trach ties into the mounting holes 140 of the second side 110, through the elongated holes of the plate, and then through the mounting holes 150 of the first side 105 so as to secure the tracheostomy tube to the patient.

At least a portion of the holder 100 may be formed using a pliable material that is non-irritating or otherwise will not harm the skin of the patient. One such exemplary material may be silk tape. Certain aspects may provide for the first side 105 to include a cushioned material so as to reduce abrasions and/or provide a more comfortable fit for the tracheostomy tube against the patient's skin. In one example, the first side 105 may include a hydrocolloid material. Other aspects may provide for the second side 110 to also include a cushioned material, e.g., the hydrocolloid material.

Other aspects may provide for the second opening 130 to include a plurality of cuts or vertically oriented slits 145. The slits 145 may be vertical and/or horizontal with respect to the holder 100 and may be provided on opposing sides of the opening 130. The slits 145 may provide even further flexibility with respect to the tracheostomy tube being used with the holder 100. For example, the slits 145 may permit the second opening of the second side 110 to be opened further so as to accommodate a connector portion of the tracheostomy tube and then to close around the smaller portion of the tube once installed. That is, the slits 145 may permit the holder 100 to be inserted over the connector, which is generally a larger diameter than the tube or cannula of the tracheostomy tube, and then to still provide secure fit against the tube. As such, the slits 145 may further prevent movement of the tracheostomy tube during use. The slits 145 may be joined to the opening 130 via a set of adjoining slits 145A.

Figure 3A:
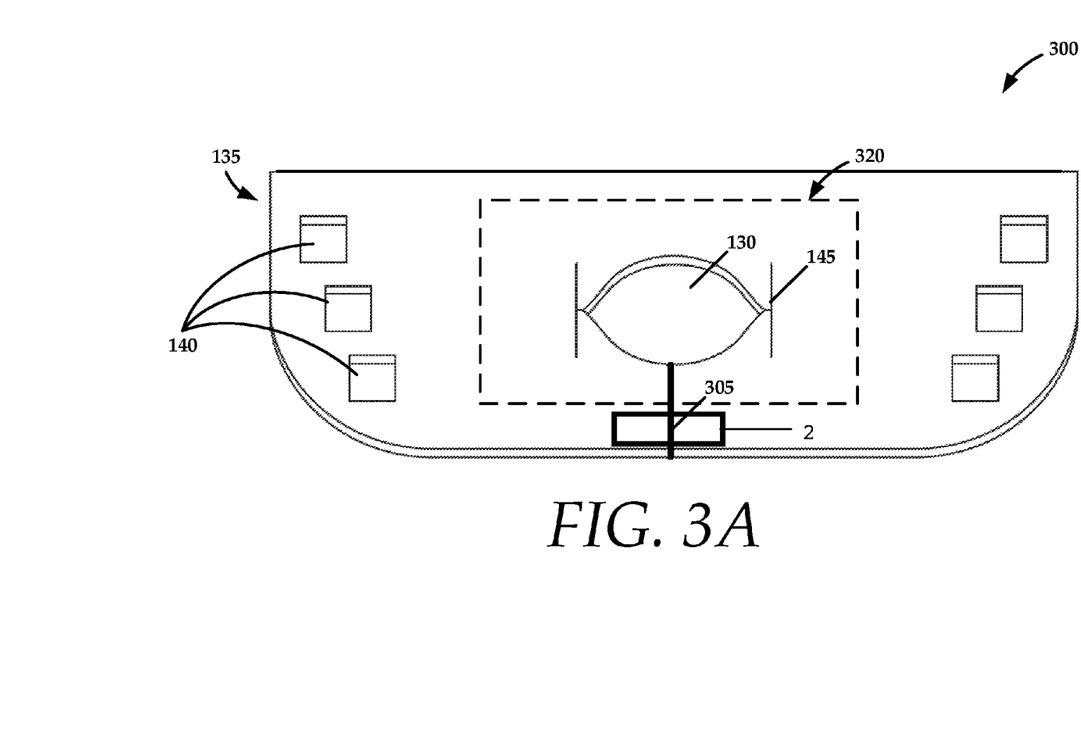
FIG. 3A is a perspective view of an exemplary tracheostomy support device installed on a tracheostomy device, constructed in accordance with the present disclosure.
Figure 3B:
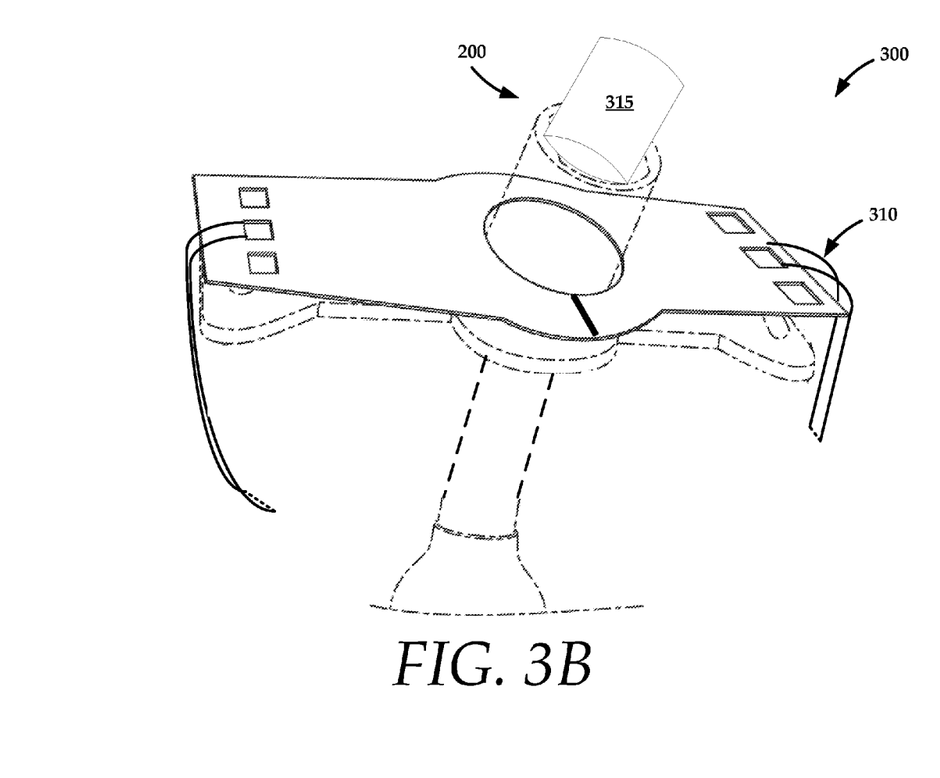
FIG. 3B is another perspective view of an exemplary tracheostomy support device of FIG. 3A without the tracheostomy device.

With respect to FIGS. 3A and 3B, a holder 300 is shown as constructed similarly to the second side 110 of holder 100 (FIGS. 1 and 2), with the exception that holder 300 includes a cut or slit 305 that allows the holder 300 to be easily removed after the holder has been mated with the tracheostomy tube 200. The slit 305 may be provided with Velcro or other means for releaseably securing the sides of the slit 305 together. Advantageously, the slit 305 allows for the holder 300 to be removed (or reinstalled) on the trach tube 200 without having to disconnect the airway hose from the trach tube 200. In some embodiments, such as in FIG. 3A, the holder 300 may include a section (or be entirely constructed from) a transparent material. For example, the holder 300 may include a transparent window 320 that provides a physician or worker a view onto the indicia of the trach tube, when the holder 300 is installed onto the trach tube 200. In some embodiments, the holder 300 includes a strip of Velcro 325 that releaseably secures to either side of the slit 305 of the second side 110.

Figure 4:
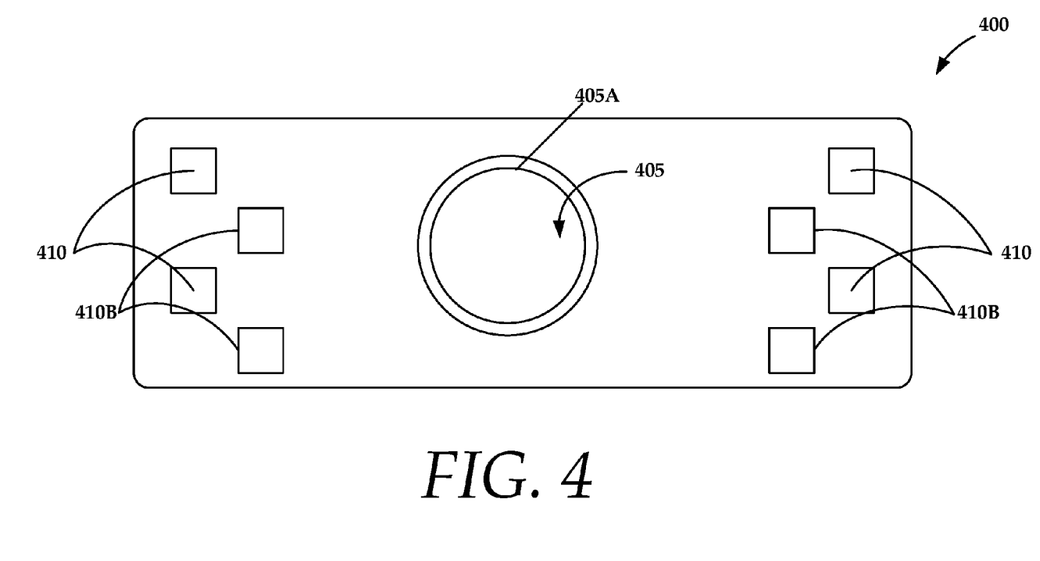
FIG. 4 is a top down view of an exemplary single strip tracheostomy support device with offset holes.

Referring now to FIG. 4, shown therein is an alternate embodiment of a tracheostomy tube holder 400, in accordance with aspects of the present disclosure. The holder 400 is similar to the holder 100 discussed above, except that the holder 400 does not include the first side 105. The holder 400 may comprise an opening 405, and a plurality of mounting holes 410 positioned on opposing sides of the holder 400 (four mounting holes 410 being shown by way of example). In some instances, some of the holes may be offset, such as with holes 410B on opposing sides of the holder 400. Generally, the holder 400 may be sized and/or shaped so as to correspond to the plate of a tracheostomy tube (e.g., the throat plate of a tracheostomy tube) such that the holder 400 can be positioned on the outside face of the tube during use. The opening 405 may be sized and/or shaped to slide over the connector portion of the tube such that the holder 400 may set flush against the outside face of the tube. The holder 400 may be sized and/or shaped such that one or more of the mounting holes 410 may be positioned on the holder 400 so as to correspond to, and align with the elongated holes of the plate. Other mounting holes 410 may be disposed past the edge of the mounting plate of the trach tube. The various locations of the mounting holes 410 permit a user to select a mounting hole 410 on opposite sides of the holder 400 so as to secure the tube to the patient at a wide variety of positions/orientations.

Figure 5:
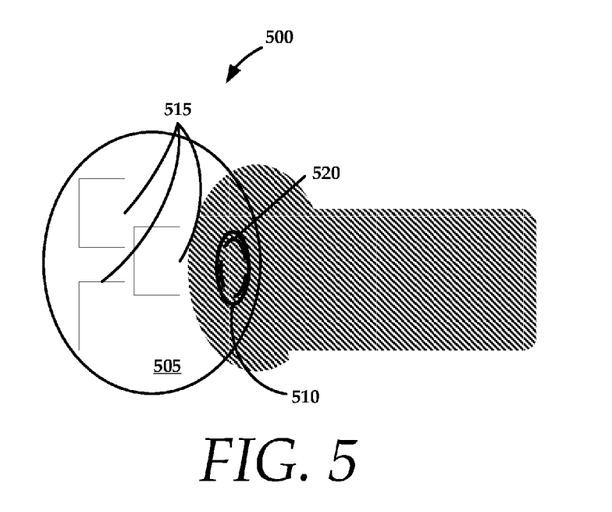
FIG. 5 is a perspective view of an exemplary tracheostomy support device extension tab.

Referring now to FIG. 5, shown therein is another alternate embodiment of a tracheostomy tube extender tab, hereinafter "tab 500," constructed in accordance with aspects of the present disclosure. The tab 500 may be a solid piece constructed of rigid, durable, bio-medical grade material that is generally sized, shaped, and/or otherwise configured to fit couple with the elongated hole 510 of a plate (e.g., into the elongated holes of a throat plate of a tracheostomy tube). Once coupled with the elongated hole 510 of the plate, the tab 500 may provide to the user a plurality of mounting holes wherein the user can select the mounting hole depending on the desired position and orientation of the tube. As shown in FIG. 5, an exemplary plate may include an elongated hole 510. The tab 500 may comprise a plurality of mounting holes 515 (with five mounting holes 515 being shown in FIG. 5, by way of example). The mounting holes 515 may extend through the tab 500 such that a trach tie may be positioned therethrough and used to secure the tracheostomy tube to the patient. As discussed above with respect to the other mounting holes, the mounting holes 515 may be formed of a variety of sizes and/or shapes, depending on the particular application of the tab 500.

The tab 500 may generally be configured with a tab or protrusion 520 that is configured to securely fit within the elongated hole 510. It is to be understood that, although FIG. 5 only shows one side of the exemplary plate 505 and one elongated hole 510, the tab 500 would generally include a complementary tab that is similar to tab 500 positioned in the elongated hole on the opposing side of the plate 505. Thus, two of the tabs would be utilized in accordance with aspects of this alternate embodiment.

Turning now to other aspects of the present disclosure, the tracheostomy tube holders 100 and 300 described herein may be utilized to create a tracheostomy tube 200 that does not include the plate 210. Thus, the holders would replace the plate 210 entirely.

For example, a tracheostomy tube 200 may not include a plate 210 having the elongated holes. The holders 100 and 300 may instead include a grommet or connector 405A (see FIG. 4) that interfaces with the tracheostomy tube circuit. The connector 405A may be a distal portion of the connector assembly, i.e., a portion of the connector positioned proximate the patient. When positioned on the tube, the user may utilize any of the opposing mounting holes to secure the tracheal tube to the patient in a variety of positions and orientations. As would be understood, the mounting holes of the holders would generally be positioned on opposing sides of the holders, rather than aligning with the elongated holes of a plate. In accordance with aspects of this embodiment, the holder may be formed of a cushioned material, e.g., the hydrocolloid material.

It is to be understood that any of the herein described holders may be sized and/or shaped so as to correspond to the size or shape of the tracheostomy tube being utilized therewith. That is, tracheal tubes may be sized depending on the age or size of the patient, e.g., neo-natal, infant, child, young adult, adult, obese adult, etc. The size of the tracheal tube would determine the size of the components forming the components of the tracheal tube, e.g., the plate size, tube diameter, tube length, etc. The herein described holders may be sized so as to correspond to the size of the tracheostomy tube it is being used with. The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A tracheostomy support device, comprising:
  a substrate comprising:
    a first side having a first opening that receives a tube of a tracheostomy tube, wherein the first side comprises a first slit that divides the first side into two sections;
    a second side having a second opening that is disposed centrally on the second side, the second opening being configured to receive a connector of the tracheostomy tube, the substrate comprising a plurality of mounting holes disposed on opposing ends of the second side, the second side comprising a second slit that extends below the second opening which allows the substrate to be removed from the connector when the connector is connected to an airway hose; and
    wherein the first and second sides are attached to one another in such a way that the first side can be folded and overlapped around a plate of the tracheostomy tube.

2. The device according to claim 1, wherein the first side comprises a plurality of mounting holes disposed on opposing ends of the first side.

3. The device according to claim 1, wherein the second side includes a pair of vertically oriented slits that are disposed on opposing sides of the opening, wherein the substrate further includes adjoining slits that join the vertical slits to the opening.

4. The device according to claim 1, wherein the plurality of mounting holes on the first and/or second side are offset from one another.

5. The device according to claim 1, further comprising a trach tie that is configured to connect with at least two mounting holes of the plurality of mounting holes on opposing sides of the substrate.

6. The device according to claim 1, further comprising the tracheostomy tube.

* * * * *